United States Patent [19]

Wah Wat

[11] 4,032,638
[45] June 28, 1977

[54] HETEROCYCLIC UREAS

[75] Inventor: Edward Koon Wah Wat, Wilmington, Del.

[73] Assignee: E. I. Du Pont de Nemours and Company, Wilmington, Del.

[22] Filed: Apr. 3, 1975

[21] Appl. No.: 564,836

Related U.S. Application Data

[60] Continuation-in-part of Ser. No. 518,871, Oct. 29, 1974, abandoned, which is a division of Ser. No. 354,871, April 25, 1973, abandoned.

[52] U.S. Cl. .................. 424/248.54; 260/244 R; 260/307 C; 424/272
[51] Int. Cl.[2] .................. A01N 9/00; A01N 9/22; C07D 265/00; C07D 273/00
[58] Field of Search .......... 260/307, 244; 424/248, 424/272, 248.54

[56] References Cited

UNITED STATES PATENTS 2,517,750  8/1950  Wilson .......................... 260/309.7
3,141,889  7/1964  Ebetino ........................ 260/307

OTHER PUBLICATIONS

Chem. Abst. 54 4539(d) (1960)–Mitsui et al. "Studies of hydrogenolysis".
Chem. Abst. 61 1851(c) (1964) 3–Aminoamidoxiimes Concalves et al.
Chem. Abst. 74 14175(j) (1971)–Crank–"1–substituted 3–(2–oxazolyl)thioureas.

*Primary Examiner*—Albert T. Meyers
*Assistant Examiner*—D. W. Robinson

[57] ABSTRACT

Ureas of the structure:

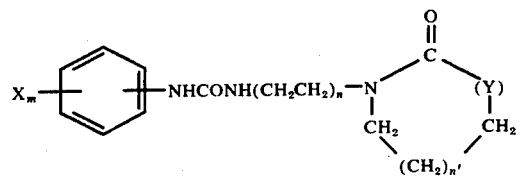

wherein
X is F or Cl or $OCH_3$;
Y is O or NH;
m is 0, 1 or 2 and n and n' each are 0 or 1 with the proviso that if n' is 1, X is not Cl and if Y is O, X is not Cl are useful in prevention of ozone damage to plants.

11 Claims, No Drawings

HETEROCYCLIC UREAS

CROSS REFERENCE TO RELATED APPLICATION

This application is a continuation-in-part of U.S. Ser. No. 518,871, now abandoned filed Oct. 29, 1974 for Edward Koon Wah Wat and entitled "Heterocyclic Ureas", which in turn is a division of application U.S. Ser. No. 354,871, filed Apr. 25, 1973 now abandoned.

BACKGROUND OF THE INVENTION

1. Field of the Invention

Certain heterocyclic ureas are useful in protecting plants from the deleterious effects of atmospheric ozone. Ozone is a common air pollutant around urban areas which has been found to damage crop plants, ornamental plants and shade and forest trees. Polluted air is estimated to cost farmers a half-billion dollars a year. Even air that contains a level of ozone below that common to urban areas reduces yields of many crops.

2. Description of the Prior Art

Ureas have been widely employed for selective biological activity. Some have been suggested for pharmacological uses, e.g. Shoeb et al. [C.A. 68, 12946e (1968)] propose 1-phenyl-3-(2-pyridylethyl) ureas to lower blood sugar. Others such as

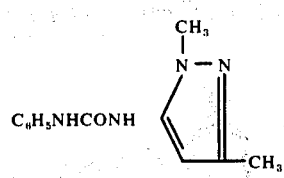

i.e., 5-(3-phenylureido)-1,3-dimethylpyrazole, have been found effective as plant defoliants in U.S. Pat. No. 3,646,059. 1-Morpholino-3-phenylurea has been shown to have cytokinin activity in a cellular assay [Bruce, Proc. Roy. Soc (London) Ser. B 165 (1966) 245-265]. Many have found application as herbicides, but none have been reported to be useful in protecting plants against atmospheric ozone.

DESCRIPTION OF THE INVENTION

The ureas of this invention have the general structure

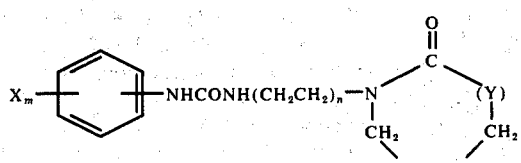

wherein
X is F, Cl or OCH$_3$;
Y is O or NH,
m is 0-2; and
n and n' are 0 or 1 with the proviso that if n' is 1, X is not Cl and if Y is O, X is not Cl, in a preferred embodiment,
X is F or OCH$_3$;
Y is O or NH;
m is 0, 1 or 2; and n and n' each are 0 or 1.
In other preferred embodiments:
X=Cl,
m=1 or 2,
n=0 or 1 and n'=0; also
X=Cl, m=1 or 2,
n=1 and n'=0.

The new compounds are usually obtained by reaction of phenyl isocyanate or a mono- or di-fluoro-, chloro-, or methoxy-substituted phenyl isocyanate with a heterocyclic amino compound of the structure

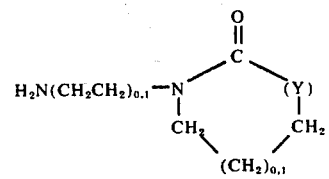

where Y is NH or O. This reaction is generally rapid and should be so conducted as to avoid local overheating.

The new compounds include, but are not limited to, those having the following structures:

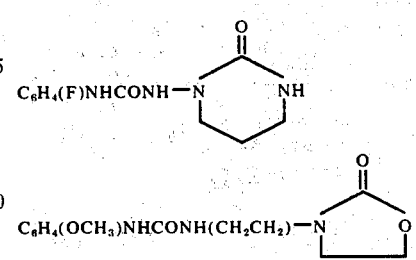

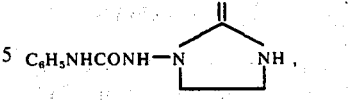

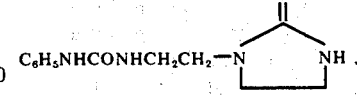

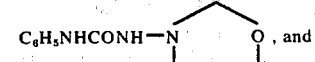

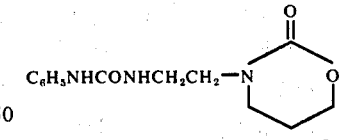

SPECIFIC EMBODIMENTS OF THE INVENTION

In the following illustrative examples all parts are by weight unless otherwise stated.

EXAMPLE 1

1-[2-(2-Oxo-1-imidazolidinyl)ethyl]-3-phenylurea
m=0,
n=1,
n'=0,
Y=NH

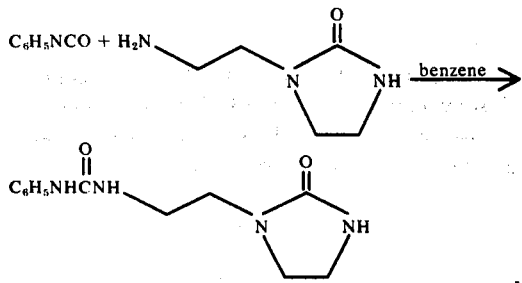

To a mixture of 6.5 g of commercially available 1-(2-aminoethyl)-2-imidazolidone and 50 ml benzene was added 5.5 ml of phenyl isocyanate. The strongly exothermic reaction was moderated by cooling to 25°. The mixture was stirred at 25° for 4 hr. It was cooled in ice and the mixture was filtered. The solid product was crystallized from 250 ml of acetone to give 6.8 g of white 1-[2-(2-oxo-1-imidazolidinyl)-ethyl]-3-phenylurea, mp 162–164°.

IR(Nujol) — 3.1 μ (NH); 5.9 (C=O)
NMR(DMSO-d$_6$) — m(1H) 8.45 δ (ArNH); m(5H) 6.7–7.5 (aromatic H); m(2H) 5.9–6.3 (NH);m(8H) 3.0–3.5 (CH$_2$).

A second crop, 1.5 g, mp 160°–163° brought the total yield to 8.3 g (67% yield).

Increased yields were obtained when the starting imidazolidone (Aldrich technical grade) was purified by dissolving in chloroform, drying over magnesium sulfate, and distilling. To 19.5 g of this purified material in 150 ml of glyme was added 16.5 ml of phenyl isocyanate with ice cooling. The clear solution was, after 18 hr at 25°, concentrated at reduced pressure. Hexane was added to the solid residue and the mixture was filtered. The solid product was suspended in 500 ml hot acetone, cooled and filtered to give 32.2 g of white solid, mp 168°–170° (86% yield).

Calcd. for C$_{12}$H$_{16}$N$_4$O$_2$: C 58.05; H 6.50; N 22.57 Found: C 58.07; H 6.72; N 21.94 58.21, 6.82 21.92.

EXAMPLE 2

1-(Tetrahydro-2-oxo-1,3-oxazin-3-yl)-3-phenylurea m=0,
n=0,
n'=1,
Y=0

Step 1 — 3-Hydrazino-1-propanol

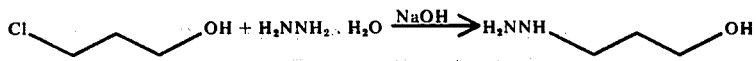

The procedure of G. Gever, J. Am. Chem. Soc. 76, 1283 (1954) was used. A mixture of 40 g of sodium hydroxide in 250 g of hydrazine hydrate was heated to 95°. The heat source was removed and 94 g of 3-chloropropanol was added at a rate necessary to maintain an internal temperature of 95°–100°. The mixture was concentrated at reduced pressure, filtered, and the solids were washed with ethanol. The filtrate was distilled through a 6-in. Vigreux column to give 49.6 g of 3-hydrazino-1-propanol as a colorless liquid, bp 91°–95° (0.2–0.5 mm) (reported bp 102°–104° (0.6 mm)).

IR(film) — 3.1 μ (NH, OH) NMR(CDCl$_3$) — m(4H) 3.9 δ (NH, OH); t(2H) 3.70, J=6 (CH$_2$O); t(2H) 2.92, J=6 (CH$_2$N); quintet (2H) 1.72, J=6 (CH$_2$).

Step 2 — 3-Amino-tetrahydro-1,3-oxazin-2-one

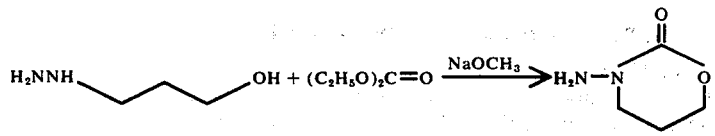

The procedure of K. Hayes, J. Am. Chem. Soc. 77, 2333 (1955) was used. A solution of sodium methoxide was prepared from 1.5 g of sodium in 15 ml of methanol. A portion (4 ml) of this reagent was added to a mixture of 18.0 g of the 3-hydrazinopropanol and 31 g of diethyl carbonate. The mixture was refluxed for 2 hr while the alcohol formed was removed by distillation. The product was distilled at reduced pressure to give 10.4 g of 3-amino-tetrahydro-1,3-oxazin-2-one as a colorless liquid, bp 105° (0.5 mm) 45% yield.

IR(film) - 3.0μ (HN); 5.9 (C=O) NMR(CDCl$_3$) - m(4H) 4.0–4.5 δ (CH$_2$O, NH$_2$); t(2H) 3.51, J=6 (CH$_2$N); m(2H) 2.10 (CH$_2$).

Step 3 — 1-(Tetrahydro-2-oxo-1,3-oxazin-3-yl)-3-phenylurea

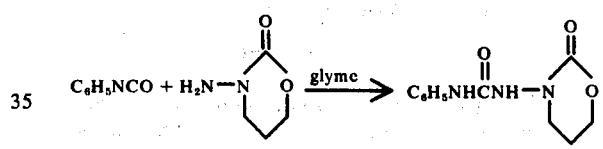

To a mixture of 5.4 g of 3-amino-tetrahydro-1,3-oxazine-2-one and 50 ml glyme was added 5.0 ml of phenyl isocyanate. After an exothermic reaction a white solid formed. The mixture was refluxed for 1 hr, cooled, diluted with hexane and filtered. The solid product was crystallized from 200 ml of ethanol to give 5.8 g (53% yield) of white cotton-like needles of 1-(tetrahydro-2-oxo-1,3-oxazin-3-yl)-3-phenylurea, mp 204°–207°.

IR(Nujol) - 3.0 μ (NH); 6.0, 5.85 (C O) NMR(DMSO-d$_6$) - m(1H) 8.80 δ (NH); m(1H) 8.30 (NH); m(5H) 6.8–7.6 (aromatic H); t(2H) 4.20, J=5 (CH$_2$O); t(2H) 3.50, J=6.5 (CH$_2$N); m(2H) 2.0 (CH$_2$).

An improved synthesis of the latter compound resulted after removal of the alcohol produced in Step 2; the residue was evacuated at 150° (0.5 mm). After cooling the slush, 300 ml of glyme was added and the mixture filtered. Concentration of the filtrate gave crude amine as a yellow oil which was not further purified. It was treated with phenyl isocyanate as in Step 3 to give a 51% overall yield (2 steps) of the urea, mp 201°–203°.

Calcd for C$_{11}$H$_{13}$N$_3$O$_3$: C, 56.16; H, 5.57; N, 17.86 Found: C, 55.95; H, 5.24; N, 17.64 56.06 5.46 17.67.

EXAMPLE 3

1-(2-Oxo-1-imidazolidinyl)-3-phenylurea m=0,
n=0,
n'=0,
Y=NH

Step 1 — 1-Amino-2-imidazolidinone

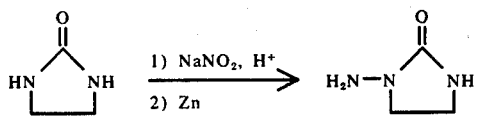

The general procedure of J. G. Michels and G. Gever, J. Am. Chem. Soc., 78, 5349 (1956) was used. To a solution of 63 g of 2-imidazolidinone in 2 l. of 2N sulfuric acid was added 50.5 g of sodium nitrite in small portions over a period of 13 min. with external cooling to maintain an internal temperature of 3°–6°. The mixture was stirred at 0° for 1.5 hr. Zinc dust (110 g) was added over a 1 hr period below 20°. The excess zinc was removed by filtration and solid barium hydroxide was added to the filtrate until a pH of 6 was attained. The white solid was removed by filtration. Aqueous (50%) sodium hydroxide was added to the filtrate until a pH of 7.9 was attained and the solid was removed by filtration. The filtrate was concentrated at reduced pressure. Methanol was added and the precipitated salts were removed by filtration. Concentration of the filtrate gave an oil which was dissolved in chloroform and dried over sodium sulfate. Upon removal of the solvent, a white solid remained which was crystallized from 25 ml of chloroform to give 5.6 g large white prisms of 1-amino-2-imidazolidinone, mp 99°–110°.

IR(Nujol) - 3.1 μ (NH); 5.9 (C=O).
NMR(DMSO) - m(1H) 6.42 δ (NH); m(2H) 4.12 (NH$_2$); m(4H) 3.21 (CH$_2$).

Step 2 — 1-(2-Oxo-1-imidazolidinyl)-3-phenylurea

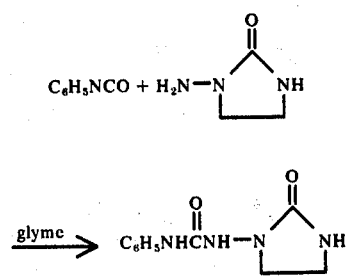

To a mixture of 3.0 g of 1-amino-2-imidazolidinone in 30 ml glyme was added 3.3 ml of phenyl isocyanate, resulting in an exothermic reaction and formation of a white solid. After 30 min. at 25°, 30 ml of hexane was added and the mixture filtered. The solids were washed well with hexane, suspended in hot ethanol, cooled, and filtered to yield 5.9 g of white solid 1-(2-oxo-1-imidazolidinyl)-3-phenylurea, mp 235°–238°.

IR(Nujol) - 3.0 μ (NH); 5.80, 5.92 (C=O).
NMR(DMSO) - m(1H) 8.75 δ, m(1H) 8.07, m(1H) 6.86 (NH); m(5H) 7.0–7.7 (aromatic H); m(4H) 3.2–3.6 (CH$_2$).

EXAMPLE 4

1-(2-Oxo-3-oxazolidinyl)-3-phenylurea m=0
n=0
n'=0
Y=O

Step 1 — 3-Amino-2-oxazolidone

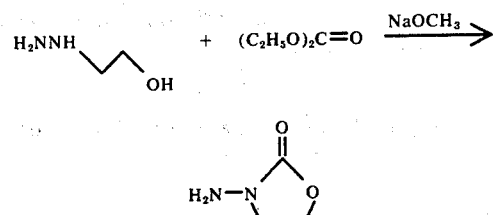

The procedure used was the same as that in Step 2 of Example 2 except 2-hydrazinoethanol was used. The crude product was a solid and could be crystallized from chloroform to give large white needles, mp 66°–68°.

IR(Nujol) - 3.0 μ (NH); 5.7 (C=O). NMR(CDCl$_3$) - m(2H) 4.16–4.50 δ (CH$_2$O); m(1-2H) 4.09 (NH$_2$); m(2H) 3.50–3.88 (CH$_2$N).

Step 2 — 1-(2-Oxo-3-oxoazolidinyl)-3-phenylurea

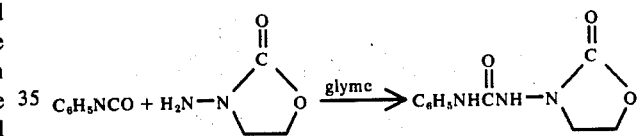

To a mixture of 6.0 g of 3-amino-2-oxazolidone in 60 ml of glyme was added 6.6 ml of phenyl isocyanate, resulting in an exothermic reaction and formation of a white solid. The mixture was refluxed for 15 min., cooled, and filtered. The solid product was crystallized from acetone to give 3.6 g of white crystals, mp 185°–190°.

IR(Nujol) - 3.11 μ (NH); 5.70 (C=O). NMR(DMSO) - m(1H) 8.97 δ, m(1H) 8.35 (NH); m(5H) 6.9–7.7 (aromatic H); m(2H) 4.2–4.6 (CH$_2$O); m(2H) 3.5–3.9 (CH$_2$N).

EXAMPLE 5

1-(Tetrahydro-2-oxo-1,3-oxazin-3-yl)-3-(2-fluorophenyl)urea m=1
X=F
n=0
n'=1
Y=O

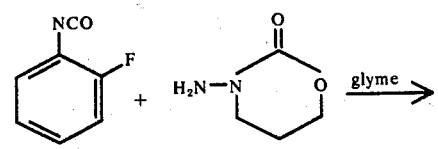

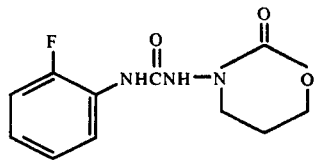

Step 3 of Example 2 was repeated using 2-fluorophenyl isocyanate. The product was crystallized from acetone to give white needles, mp 190°–193°. Spectra were similar to that in Example 2.

EXAMPLE 6

1-(Tetrahydro-2-oxo-1,3-oxazin-3-yl)-3-(4-fluorophenyl)urea $m=1$
$X=F$
$n=0$
$n'=1$
$Y=0$

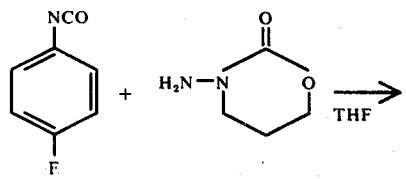

Using the general procedure of the preceding example with 4-fluorophenyl isocyanate, this isomer was prepared, mp 216°–219°.

EXAMPLE 7

1-(Tetrahydro-2-oxo-1,3-oxazin-3-yl)-3-(3-fluorophenyl)urea $m=1$
$X=F$
$n=0$
$n'=1$
$Y=0$

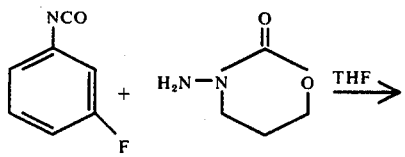

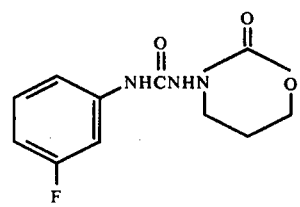

When 3-fluorophenyl isocyanate was used in the procedure of Example 6, the 3-isomer was prepared, mp 199°–203°.

EXAMPLE 8

1-(2-Tetrahydro-2-oxo-1,3-oxazin-3-yl)-3-(2,4-dimethoxyphenyl)urea $m=2$
$X=OCH_3$
$n=0$
$n'=1$
$Y=0$

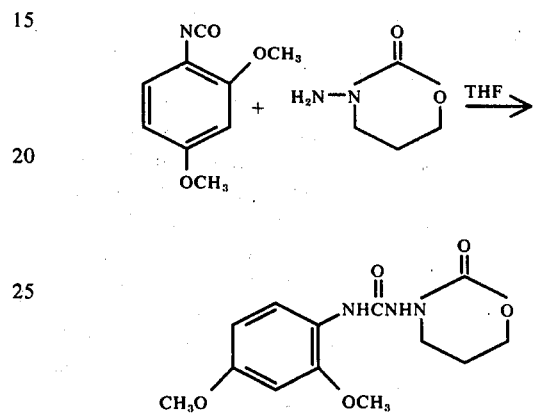

The above compound was similarly prepared using 2,4-dimethoxyphenyl isocyanate. The solid product was crystallized from glyme, mp 183°–190°.

EXAMPLE 9

1-[2-(2-Oxo-3-imidazolidinyl)-ethyl]-3-(4-chlorophenyl)urea $X=Cl$
$Y=NH$
$m=1$
$n=1$
$n'=0$

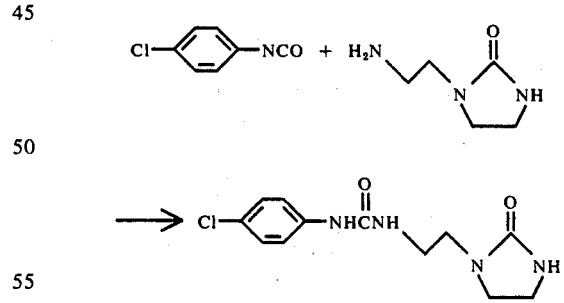

To a mixture of 6.5 g of 1-(2-aminoethyl)-2-imidazolidone in 65 ml of tetrahydrofuran was added 8.0 g of p-chlorophenyl isocyanate with ice cooling to maintain an internal temperature of 25° (exothermic reaction). The mixture was stirred at 25° for 18 hr during which a white solid formed. The mixture was filtered and the solids were washed with petroleum ether. The solid product was crystallized from 100 ml acetone to give 7.5 g of white crystals, m.p. 132°–135° C.

IR(Nujol) — 2.9 μ (NH); 5.9 (C=O).

NMR(DMSO — d₆) — m(1H) 8.65 δ (NH); AB pattern (4H) 7.33 (aromatic H); m(2H) 6.0–6.4 (NH); m(8H) 3.2 (CH₂N).

Calcd for C₁₂H₁₅N₄O₂Cl: C, 50.98; H, 5.35; N, 19.82. Found: C, 51.63; H, 5.35; N, 19.30. C, 51.65; H, 5.42; N, 19.47.

EXAMPLE 10

1-[2-(2-Oxo-3-imidazolidinyl)-ethyl]-3-(2,4-dichlorophenyl)urea

X=Cl
Y=NH
m=2
n=1
n'=0

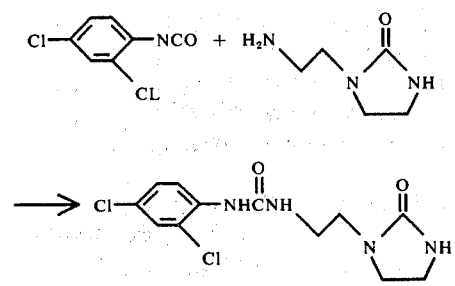

In like manner, from 4.3 g of the amine, 6.3 g, 2,4-dichlorophenyl isocyanate and 50 ml THF was obtained a solid product which was crystallized from 100 ml ethanol to give 7.2 g of white needles, mp 188°–191° C.

IR(Nujol) — 2.9 μ (NH); 5.94 (C=O).

NMR(DMSO — d₆) — m(2H) 7.9–8.1 δ (1NH, 1 aromatic H); m(3H) 6.8–7.3 (1NH, 3 aromatic H); m(1H) 6.14 (1NH); m(8H) 3.2 (CH₂N).

Calcd for C₁₂H₁₄N₄O₂Cl₂: C, 45.44; H, 4.45; N, 17.66. Found: C, 46.01; H, 4.35; N, 16.90. C, 45.86; H, 4.49; N, 17.08.

When 3-chloropropanol is reacted with 1-(2-aminoethyl)-3-phenylurea and the resulting 1-[2-(3-hydroxypropylamino)ethyl]-3-phenylurea is reacted with diethyl carbonate according to the general processes of steps 1 and 2 of Example 2, there is obtained 1-[2-(tetrahydro-2-oxo-1,3-oxazin-3-yl)-ethyl]-3-phenylurea.

Repetition of the general process of Example 1 except using a fluorophenyl isocyanate (Examples 5–7) or 2,4-dimethoxyphenyl isocyanate (Example 8) gives the corresponding fluoro- or dimethoxyphenyl 2-(2-oxo-1-imidazolidinyl)-ethylureas. Reaction of 1-amino-2-imidazolidinone (see Example 3) with the above substituted isocyanates or with chlorinated phenyl isocyanates (Examples 9 and 10) gives the corresponding fluoro-, chloro-, dichloro- or dimethoxyphenyl 2-oxo-1-imidazolidinylureas. Isomeric difluorophenyl and methoxyphenyl isocyanates can be substituted for phenyl or substituted phenyl isocyanates in the preceding examples to give 3-difluorophenyl and 3-methoxyphenyl 1-(2-oxotetrahydro-1,3-oxazin-3-yl)ureas, 1-(-2-oxo-1-imidazolidin-yl)ureas, 1-(2-oxo-1-tetrahydrooxazinyl)ureas and 1-(2-oxo-1-tetrahydropyrimidyl)ureas.

The compounds of the invention are useful to protect plants against the harmful effects of ozone. The amount of compound required for optimum effects will depend on the particular crop and environment under which it is growing. Within the meaning of this case, the amount of compound necessary to accomplish protection against ozone will be termed an "effective amount". Normally, the rate at which the compound is applied will range from 0.02 to 3.0 kilogram per hectare although higher rates can be used. One skilled in the art will be able to select the appropriate rate of application for any particular situation. Plants that can be protected from the deleterious effects of ozone include oranges, lemons, tobacco, grapes, potatoes, tomatoes, soybeans, corn, lettuce, alfalfa and ornamental plants.

The compounds of the present invention can be used in the form of compositions which are prepared by admixing at least one of the active compounds with an inert diluent, such as pest control adjuvants or modifiers, to provide compositions in the form of dusts, water-dispersible powders, high-strength concentrates, and aqueous or organic dispersions. Thus, the compounds of this invention can be used with a carrier or diluent agent such as a finely divided solid, an organic liquid, water, a wetting agent, a dispersing agent, an emulsifying agent, or any suitable combination of these.

The compositions, especially liquids and wettable powders, may contain as a conditioning agent one or more surface-active agents, sometimes called surfactants, in amounts sufficient to render a given composition containing the compounds of this invention readily dispersible in water or in oil.

The following examples illustrate the use of the above compounds to inhibit ozone damage to plants.

EXAMPLE A

Pinto beans (*Phaseolus vulgaris*) were grown in vermiculite in 4-in. plastic pots under 12-hr days with 2200 foot-candles illumination (fluorescent plus incandescent). The daytime temperature and relative humidity were 75° F. and 75%, respectively. At night they were 65° C. and 85%. Thirteen days after planting a representative plant was sprayed with a 500 ppm solution of 1-(tetrahydro-2-oxo-1,3-oxazin-3-yl)-3-phenylurea (Ex. 2). The spraying solution also contained 3.5% glycerol and 175 ppm of an alkyl polyethylene oxide surface-active agent ("Tergitol" 15-S-12). Two other plants were sprayed with the glycerol-surface active agent solution without the compound and two additional plants were not sprayed.

On the following day, these plants were exposed to 60 pphm (parts per hundred million) O₃ for 2½ hr in a fumigation chamber having about one air change a minute. 2 days later the five plants were examined. The ozone had caused extensive damage to the two primary leaves of the unprotected plants. Damage consisted of brown lesions and bifacial tissue collapse. In the two unsprayed plants the damaged area made up 90% and 100% of the leaf area respectively. The plants sprayed with glycerol and surface active agent only were damaged to the extent of 80% and 85% of the leaf surface. The plant treated with the heterocyclic urea suffered no visible damage. This plant was returned to the fumigation chamber and again exposed to 60 pphm ozone for 2½ hr. When the plant was examined two days later there was still no visible damage. A fresh unsprayed control plant, which was fumigated along with the test plant, was damaged to the extent of 80% of its leaf area.

EXAMPLE B

Conditions employed were similar to Example A except the test plant was sprayed with a 500 ppm solution of 1-[2-(2-oxo-1-imidazolidinyl)ethyl]-3-phenylurea. (Ex. 1). Two days after fumigation the foliar damage was 10%. The plant was refumigated. Two days later the damage was still only 15%.

EXAMPLE C

The general procedure of Example A was repeated except a 500 ppm solution of 1-(2-oxo-1-imidazolidinyl)-3-phenylurea (Ex. 3) was sprayed on the plant 24 hr prior to fumigation. 2 days after fumigation there was no visible injury. The plant was refumigated and after two more days was again inspected. No damage was observed.

EXAMPLE D

The procedure of Example A was followed except that a 500 ppm solution of 1-(tetrahydro-2-oxo-1,3-oxazin-3-yl)-3-(2-fluorophenyl)urea (Ex. 5) was sprayed on the plant before fumigation. 2 days after fumigation there was no observable damage. The plant was refumigated. 2 days later the visible damage was only 10% of the leaf surface.

EXAMPLE E

The procedure of Example A was followed except that a 500 ppm solution of 1-(tetrahydro-2-oxo-1,3-oxazin-3-yl)-3-(3-fluorophenyl)urea (Ex. 7) was sprayed on the plant before fumigation. 2 days after fumigation the foliar damage was 10%. The plant was refumigated. 2 days later only 15% of the leaf area was damaged.

EXAMPLE F

The procedure of Example A was followed except that a 500 ppm solution of 1-(tetrahydro-2-oxo-1,3-oxazin-3-yl)-3-(4-fluorophenyl)urea (Ex. 6) was used. 2 days after fumigation there was no visible damage. The plant was refumigated. 2 days later the foliar damage was only 15%.

EXAMPLE G

The procedure of Example A was followed except that a 500 ppm solution of 1-(tetrahydro-2-oxo-1,3-oxazin-3-yl)-3-(2,4-dimethoxyphenyl)urea (Ex. 8) was sprayed on the plant before fumigation. Two days after fumigation the foliar damage was only 5% the leaf area. The plant was fumigated again. 2 days later the damage affected only 15% of the leaf surface.

As mentioned, the method of application to inhibit ozone damage of plant foliage can very. Preferably, the compounds are applied as a foliar spray in aqueous media at a concentration of about 500 ppm. However, compounds of Examples A and B give good protection when applied at concentrations of 50 ppm. For foliar applications, it is preferred that a conventional wetting agent be present, e.g. 50–500 ppm of a nonionic detergent to aid in uniform coverage.

In place of foliar application, the compounds can be applied to soil absorption through the roots. The latter may provide effectiveness over a greater length of time than generally effective as a foliar spray. Foliar applications are preferred to be within a week before exposure to atmosphere containing a substantial amount of ozone.

EXAMPLE H

Pinto beans (*Phaseolus vulgaris*) were grown in vermiculite in 4-in. plastic pots under 16-hr days with 2000 foot-candles illumination (fluorescent plus incandescent). The temperature and relative humidity were 75° F and 75% during the day and 65° F and 85% at night. Twelve days after planting a representative plant was sprayed to run-off with a 500 ppm solution of a compound of this invention 1-[2-(2-oxo-3-imidazolidinyl)ethyl]-3-(4-chlorophenyl)urea in water containing 3.5% glycerol and 175 ppm of an alkyl polyethylene oxide surface-active agent. Another plant was sprayed with the glycerol solution of surface-active agent and a third plant was not treated at all.

On the following day these three plants were exposed to 0.65 ppm ozone for 2½ hr in a chamber whose illumination, temperature and humidity matched that described above. Two days later the three plants were given a second exposure to ozone identical with the first.

On the following day the primary leaves of the three plants were rated for ozone injury. The two plants not treated with the chlorinated heterocyclic urea had brown lesions and bifacial tissue collapse over 55–75% of the leaf surface. The plant treated with the compound of this invention had damage over only 5% of its leaf surface. This is a dramatic demonstration of the power of this compound to protect a plant from injury by two exposures to a high concentration of ozone.

I claim:

1. A compound of the formula

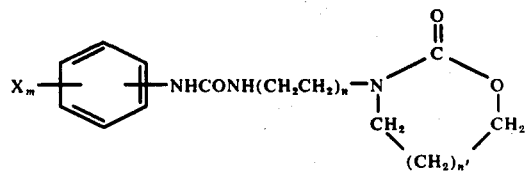

wherein
X = F[,Cl] or $OCH_3$;
$m$ = 0, 1 or 2; and
$n$ and $n'$ each = 0 or 1.

2. The compound of claim 1 wherein $n = 1$ and $n' = 0$.

3. The compound of claim 1 wherein $n = 1$ and $n' = 1$.

4. The compound of claim 1 wherein $n = 0$ and $n' = 0$.

5. The compound of claim 1 wherein $n = 0$ and $n' = 1$.

6. The compound of claim 1, 1,-(2-oxo-3-oxazolidinyl)-3-phenylurea.

7. The compound of claim 1, 1-(tetrahydro-2-oxo-1,3-oxazin-3-yl)-3-phenylurea.

8. A composition to protect plants against atmospheric ozone comprising an amount sufficient to protect plants against said ozone of a compound of the formula

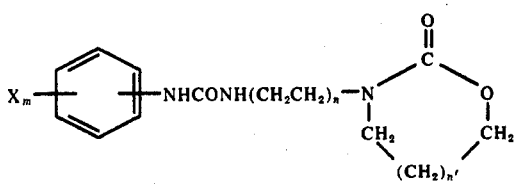

wherein

X = F[,Cl,] or OCH$_3$;

m = 0, 1 or 2; and n and n' each = 0 or 1 and a suitable carrier therefor.

9. A composition to protect plants against atmospheric ozone comprising the compound of claim 6 and a suitable carrier therefor.

10. The method of protecting plants against atmospheric ozone comprising applying to the plants an effective amount of a compound of the formula:

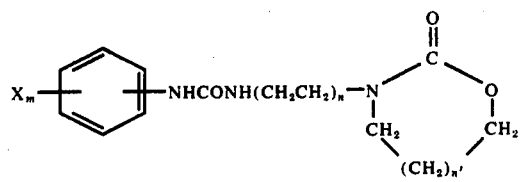

wherein

X = F, or OCH$_3$;

m = 0, 1 or 2; and n and n' each = 0 or 1 and a suitable carrier therefor.

11. The method of protecting plants against atmospheric ozone comprising applying to the plant an effective amount of the compound of claim 6.

* * * * *